US007604759B2

(12) United States Patent
Gubler et al.

(10) Patent No.: US 7,604,759 B2
(45) Date of Patent: Oct. 20, 2009

(54) PROCESS FOR PRODUCING DENTAL PROSTHESES

(75) Inventors: Daniel Gubler, Fällanden (CH); Urs Brodbeck, Erlenbach (CH)

(73) Assignee: Xawex AG, Ebmatingen (CH)

(*) Notice: Subject to any disclaimer, the term of this patent is extended or adjusted under 35 U.S.C. 154(b) by 80 days.

(21) Appl. No.: 10/551,838

(22) PCT Filed: Apr. 3, 2004

(86) PCT No.: PCT/CH2004/000212

§ 371 (c)(1),
(2), (4) Date: Jul. 20, 2006

(87) PCT Pub. No.: WO2004/086999

PCT Pub. Date: Oct. 14, 2004

(65) Prior Publication Data
US 2007/0275352 A1    Nov. 29, 2007

(30) Foreign Application Priority Data
Apr. 4, 2003    (CH) .................................... 619/03

(51) Int. Cl.
*A61C 13/00* (2006.01)
(52) U.S. Cl. .............. 264/16; 264/667; 428/542.8; 428/64.1; 428/702; 428/156; 433/223
(58) Field of Classification Search ............ 409/84, 409/85, 93, 94, 96, 98, 99, 100, 103, 104, 409/105, 106, 108, 113, 114, 116, 124, 225, 409/219; 433/24, 215, 218, 223; 700/163; 428/542.8, 64.1, 702, 156, 701; 264/16, 264/603, 604, 667, 681; 269/309, 257; 279/141, 279/145; 83/465
See application file for complete search history.

(56) References Cited

U.S. PATENT DOCUMENTS

| 4,443,394 | A | * | 4/1984 | Ezis ........................... 264/659 |
|---|---|---|---|---|
| 4,885,199 | A | * | 12/1989 | Corbin et al. ................ 428/113 |
| 5,215,948 | A | * | 6/1993 | Egerton et al. .............. 501/134 |
| 5,342,696 | A | * | 8/1994 | Eidenbenz et al. ....... 428/542.8 |
| 5,820,960 | A | * | 10/1998 | Kwon ........................ 428/64.1 |
| 6,165,925 | A | * | 12/2000 | Rieger ........................ 501/103 |
| 6,769,912 | B2 | * | 8/2004 | Beuschel et al. ............ 433/163 |
| 6,902,790 | B1 | * | 6/2005 | Hata et al. .................. 428/141 |
| 6,905,293 | B1 | * | 6/2005 | Filser et al. .................... 409/84 |
| 7,077,391 | B2 | * | 7/2006 | Filser et al. ................. 269/287 |
| 7,157,096 | B2 | * | 1/2007 | Zhang et al. ................ 424/422 |
| 2002/0155412 | A1 | * | 10/2002 | Panzera et al. ............. 433/223 |
| 2003/0031984 | A1 |   | 2/2003 | Rusin et al. |
| 2003/0125189 | A1 | * | 7/2003 | Castro et al. ................ 501/127 |
| 2003/0157357 | A1 |   | 8/2003 | Rusin et al. |
| 2004/0067839 | A1 | * | 4/2004 | Nawa et al. ................. 501/105 |

(Continued)

FOREIGN PATENT DOCUMENTS
JP    2003-506191 T    2/2003

(Continued)

OTHER PUBLICATIONS
Merriam-Webster's Collegiate Dictionary, 10th ed., p. 334, definition of "disk", copyright 1998.*

(Continued)

*Primary Examiner*—Erica E Cadugan
(74) *Attorney, Agent, or Firm*—Buchanan Ingersoll & Rooney PC

(57) ABSTRACT

In the process for producing dental phostheses such as bridges, crowns implants, etc. from ceramic material, production is carried out at least by way of one CAD/CAM machining station. The ceramic material to be worked consists of an unsintered disk-shaped blank or one which has not been subjected to final sintering, working of the blank into dental prostheses being undertaken at a right angle or quasi-right angle to the parallel or quasi-parallel surfaces of the blank.

13 Claims, 4 Drawing Sheets

U.S. PATENT DOCUMENTS

| | | | |
|---|---|---|---|
| 2006/0115794 A1* | 6/2006 | Sager | 433/218 |
| 2007/0269768 A1 | 11/2007 | Rusin et al. | |
| 2009/0023112 A1* | 1/2009 | Ganley et al. | 433/215 |
| 2009/0130634 A1* | 5/2009 | Ganley et al. | 433/206 |

FOREIGN PATENT DOCUMENTS

| | | | |
|---|---|---|---|
| WO | 44 36 231 A1 | 11/1995 | |
| WO | WO 00/40206 A1 | 7/2000 | |
| WO | WO 01/12097 A1 | 2/2001 | |
| WO | WO 01/13862 A1 | 3/2001 | |
| WO | WO 02/45614 A1 | 6/2002 | |

OTHER PUBLICATIONS

Printout from www.dentalzirconia.com, 2 pages, no date established prior to Jun. 2009.*

* cited by examiner

PROCESS FOR PRODUCING DENTAL PROSTHESES

TECHNICAL FIELD

This invention relates to a process for producing dental prostheses such as bridges, crowns, implants, etc. from ceramic material, production being carried out at least by way of a CAD/CAM machining station or other cutting machining station. It also relates to a machining station for producing dental prostheses such as bridges, crowns, implants, etc., the machining station being built as a cutting, guided and/or CAD/CAM-type system, and a blank for use with such a machining station.

BACKGROUND

WO 99/47065 discloses a process and a blank for producing artificial crowns and/or bridges which can be matched to a tooth stump which had been prepared beforehand. The three-dimensional outer and inner surface of a positive cast of the base frame for crowns and/or bridges are scanned and digitized. The determined data are linearly increased in all 3-dimensional directions by a factor which compensates exactly for the sintering shrinkage, are transmitted to the control electronics of at least one machine tool for working blanks of porous ceramic, and suitable tool paths are derived from it. By means of control commands for tools the material is removed from the blank, decoupled in time from the digitization, until there is an enlarged embodiment of the positive cast. This enlarged base frame is sintered to the base frame with direct end masses. In doing so powders or colloids for producing the blank are processed by way of known methods of ceramic shaping into green blanks. This publication furthermore emphasizes that for production engineering reasons simple geometrical shapes such as cylinders or cuboids are made available for the blanks. Consequently the teaching for technical action from this publication is based on cylindrical or cuboidal blanks which are pivotally clamped between two shafts. For reasons of production these blanks have a short length so that they are suited solely to be useful for only a single dental prosthesis consisting of few elements. It is furthermore conspicuous here that machining takes place on the surface perpendicular to the lengthwise axis of these cylindrical or cuboidal blanks; this inevitably leads to extensive removal of ceramic material and wear of the machining tools, especially when the blanks are of cylindrical shape. Furthermore, it is obvious here that the working of these blanks requires longer milling times. These important limitations greatly reduce the acceptance of the technology proposed here.

SUMMARY

The invention intends to provide a remedy here. The object of the invention as is characterized in the claims is to propose a process which can permanently eliminate all the aforementioned disadvantages. In particular, the object is to suggest a process based on a system which for the first time enables a wide range of dental prostheses with ceramic material, these prostheses being able to be produced by the most simple operation of the hardware and software which belongs to the process at low production costs.

Viewed in this way, the first focus of the invention is to make available a ceramic material which can be worked for dental prostheses, with a configuration which can eliminate the possibilities which limit the prior art. The ceramic material as claimed in the invention consists of a disk-shaped or puck-shaped blank which for its part is obtained from a compact which is formed in fully isostatic or quasi-isostatic pressing.

The blank obtained by fully isostatic or quasi-isostatic pressing is of a cylindrical or quasi-cylindrical shape and has a relatively great length with a relatively large diameter, preferably greater than 50 mm, such that at right angles to its axis a greater number of disk-shaped blanks of varied thickness can be separated in parallel cutting technology.

In itself, the blank can also consist of a round or quasi-round disk of variable diameter and thickness or of some other geometrical external shape of variable external dimension and thickness.

The fully isostatic pressing is characterized in that the pressure is applied on all sides, i.e. also in the axial direction, to the cylindrical or cylinder-shaped blank, by which a maximized, homogenous internal density of the ceramic material over the entire machining surface is achieved. This high-quality homogeneity has the advantage that the subsequent final sintering process for the dental prostheses which has been produced, independently of the sector of the blank from which they originate, is characterized by exact, predefinable shrinkage; this is reflected in the exact dimensional stability of the final product.

As claimed in the invention, it is furthermore ensured that the disk-shaped blanks before machining into dental prostheses are either in a defined unsintered form, or are first thermally treated according to certain criteria such that they are machined as blanks which have not yet been finally sintered. A homogeneous, defined physical structure of the blanks is the prerequisite for the shrinkage in the final sintering process being exactly fixed beforehand in conjunction with the produced dental prostheses, regardless of whether this final sintering process is conducted up to the absolute specific weight of the ceramic material or is to remain under it, as required.

One important advantage of the invention is that the large area of the blank easily allows accommodation of large dental prostheses which extend up to 14-element bridges, the accommodation of several prostheses at once for machining being possible, so that it is obvious that longer milling operations without material changing is possible with these blanks. This results in that the retooling time is distributed among a host of prostheses; this highly benefits the production costs of these products.

Another important advantage of the invention is that production costs are further minimized in that the maximized diameter of the blanks allows better use of the material in the arc area such that optimized placement of the machining operations which are to be carried out is possible at any time, even subsequently for an already highly worked blank.

Another important advantage of the invention is that, depending on the prosthesis, different blank thicknesses can be used, for example thin blanks for crowns, thicker blanks for tall bridges.

Another important advantage of the invention is that an exact prediction about the shrinkage which is to be expected in the final sintering process becomes possible by classification of the blanks.

Basically one important advantage of the invention, as already indicated above, is that at this point machining takes place, not on the periphery of the cylindrical or cuboidal blank, but on the plane surfaces of the disk-shaped blank as claimed in the invention, with which for the blanks as claimed in the invention shorter machining times (milling times) result, since less material need be removed compared to cylindrical or cuboidal blanks.

Advantageous and feasible developments of the object as claimed in the invention are identified in the other claims.

One embodiment of the invention is detailed below using the drawings. All elements which are not important to the immediate understanding of the invention have been omitted. The same elements are provided with the same reference numbers in the different figures.

BRIEF DESCRIPTION OF THE DRAWING FIGURES

DETAILED DESCRIPTION OF THE PREFERRED EMBODIMENTS

Figure 1:
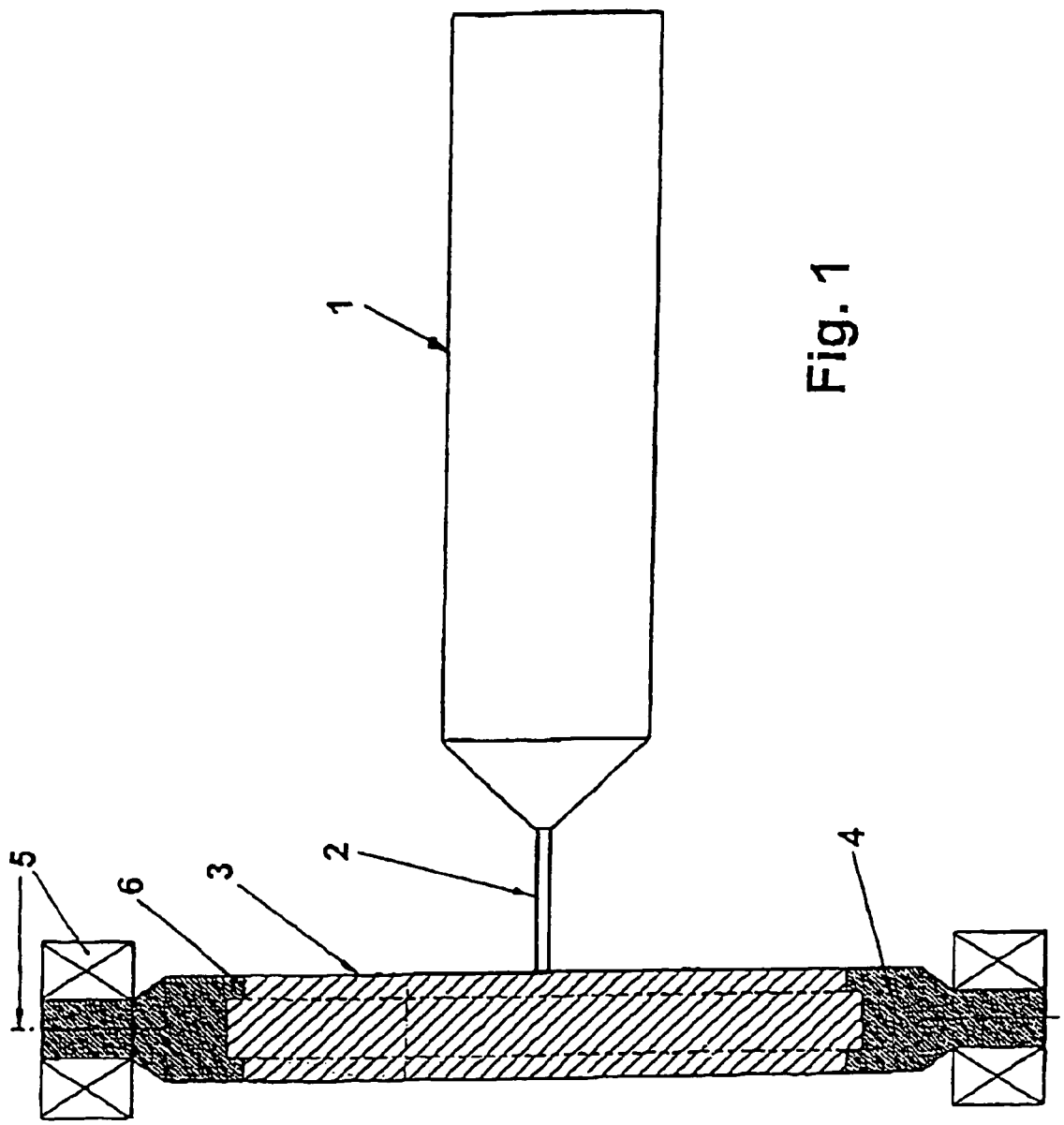
FIG. 1 shows the most important features in the working of the blank.

FIG. 1 shows the mechanical disposition in the machining of a blank 3. As already repeatedly described above, this blank 3 has the shape of a disk and is clamped vertically in a holding device 4 within at least one CAD/CAM machining station, with which a spindle traversing motor 1 with the pertinent cutters 2 works the surface of the blank 3 in the horizontal direction. The blank 3 is pivotally clamped in a holding device 4 by way of the axle 5, the blank 3 in the peripheral direction having concentric grooves 6 on which the holding device 4 acts nonpositively. This horizontal machining of the blank 3 is designed such that the occlusal and cavity shapes of the respective dental prosthesis are worked. To do this, the optimum controlled working dispositions are predetermined and implemented. Machining of the blanks can be accomplished not only by CAD/CAM, but also be other cutting systems. The sequences which precede this machining can be briefly described as follows:

The gum is modelled onto the gypsum cast with a plastic material. The intermediate element with the connecting bars (see FIG. 3 in this respect) is modelled with wax such that it can be easily removed. The procedure is similar for a bridge with several intermediate elements. First, the modelled gypsum cast is read in with a laser, the data are tailored with software tools, these data then being read into the CAD. Besides the input of wall thickness and cement gap, no other structural interventions are necessary. Then the holding bars are placed. For a blank with a diameter of roughly 100 mm up to 20 units can be worked (see in this respect FIG. 2). The NC milling data are automatically generated. Of course software suitable for this purpose is used and continuously subjected to an improvement process. The entire system easily allows implementation of specific customer wishes. The specifications of the blank as claimed in the invention relating to its production for fully isostatic or quasi-isostatic pressing of a compact and with respect to the unsintered state or the state not finally sintered have already been detailed in the section "Description of the Invention". The compact produced by fully isostatic or quasi-isostatic pressing is externally turned cylindrically as required into a cylindrical solid body before it is cut into blanks in the manner of disks. Of course a CAD/CAM machining station can also be imagined in which the blank is arranged horizontally and the spindle traversing motor then operates vertically.

Figure 2:
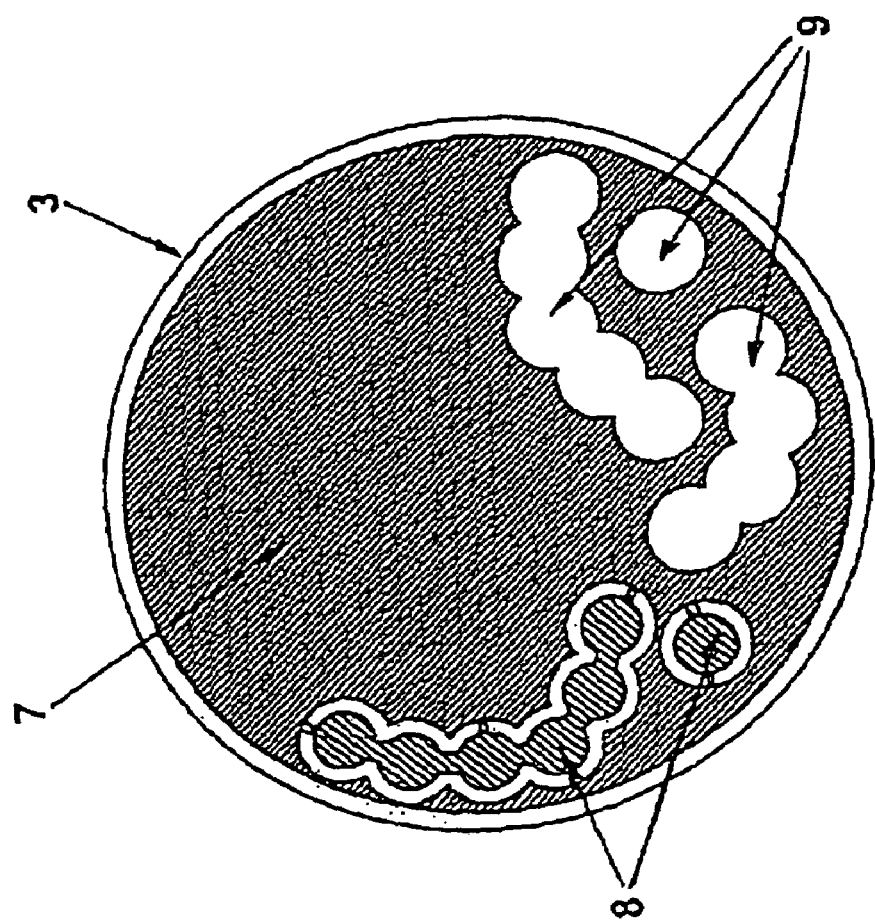
FIG. 2 shows the production of dental prostheses from a blank.

FIG. 2 shows the blank 3 with its free, machinable surface 7, in which milled prostheses 8 as well as bridges and crowns 9 which have already be detached from it are apparent.

Figure 3:
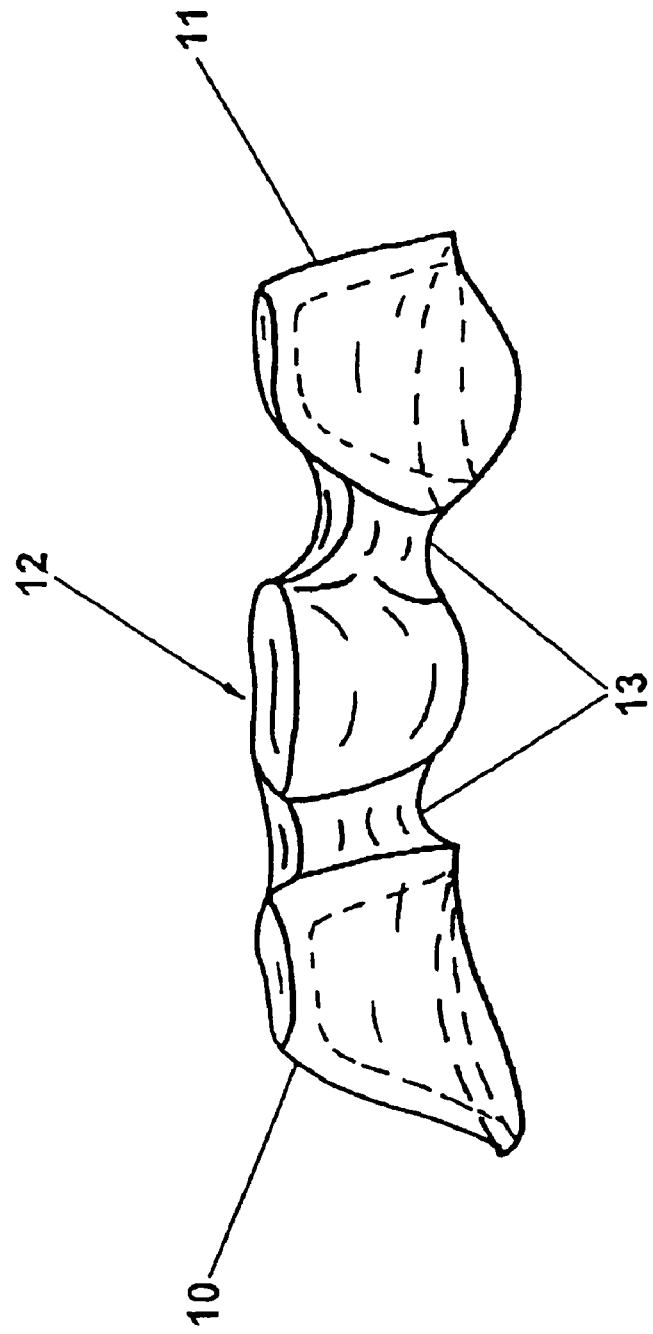
FIG. 3 shows a 3-element bridge.
Figure 4:
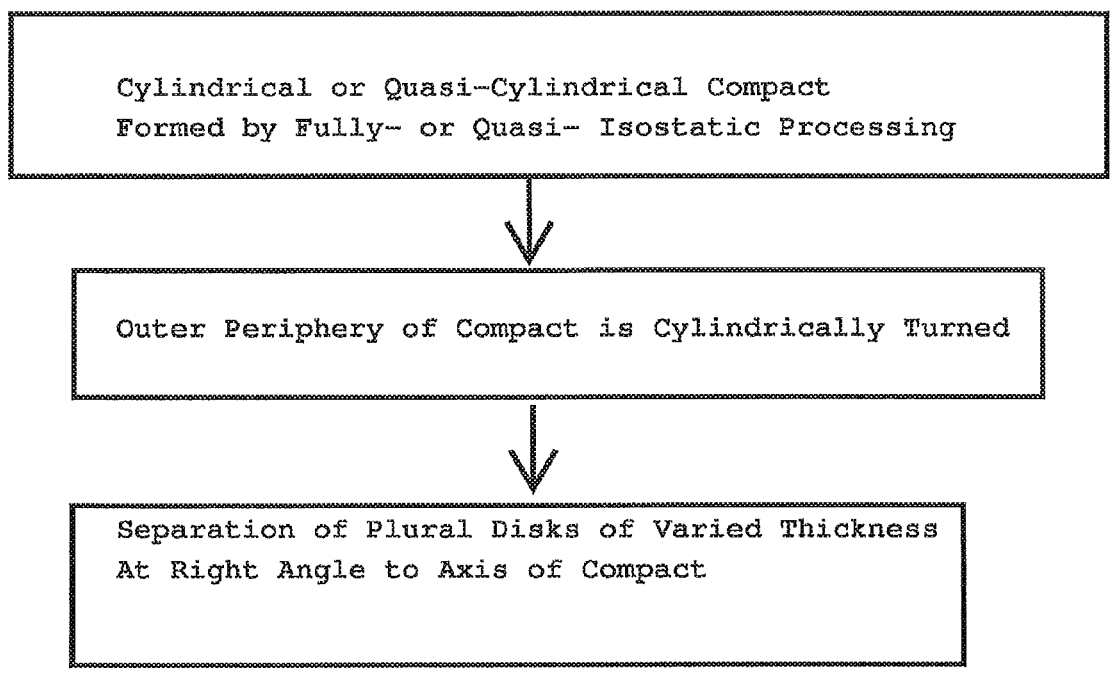
FIG. 4 shows a process for producing a blank.

FIG. 3 shows a machined, 3-element bridge consisting of two end-side crowns 11, an intermediate element 12 and two intermediate connecting bars 13. The bridge is delivered to a final sintering process after it is detached from the blank. In order to ensure optimism process accuracy here, a high temperature tube furnace is used which represents an optimum choice based on its reproducible high accuracy. With an output of more than 4 KW and a reproducible accuracy of +/−2° C. this sintering furnace forms the last process step of the production process. Prostheses produced from zirconium oxide are distortion-free at more than 1500° C. within 16 hours and are sintered to the absolutely attainable specific weight of 6.075 g/mm$^3$. If the absolutely attainable specific weight in the dental prosthesis is not desired for any reason, the temperature and the residence time in the sintering furnace can be matched accordingly.

The invention claimed is:

1. A blank for producing dental prostheses, wherein the blank is made from ceramic material being in unsintered form or being not finally sintered and wherein the blank is configured as a round or quasi-round disk with a diameter greater than 50 mm and wherein the blank comprises in the peripheral direction thereof means for its force-locking clamping in a holding device of a CAD/CAM machining station.

2. A blank as claimed in claim 1, wherein the blank has a diameter of at least 80 mm.

3. A blank as claimed in claim 1, wherein the blank has a thickness of greater than 10 mm.

4. A blank as claimed in claim 1, wherein said means for its force-locking clamping comprises at least one concentric groove.

5. A blank as claimed in claim 1, comprising a fully isostatic or quasi-isostatic pressed ceramic material.

6. A blank as claimed in claim 1, wherein said ceramic material comprises zirconium oxide.

7. A blank as claimed in claim 1, wherein said dental prostheses comprise bridges, crowns or implants.

8. A process for producing a blank according to claim 1, wherein a cylindrical or quasi-cylindrical compact is formed by fully isostatic or quasi-isostatic pressing of ceramic material and wherein the blank is one of a plurality of disk-shaped blanks of varied thickness that are separated at a right angle to an axis of the compact.

9. A process as claimed in claim 8, wherein an outer periphery of the compact is cylindrically turned.

10. A process as claimed in claim 8, wherein the blanks are of at least 80 mm diameter and are produced in fully isostatic pressing.

11. A process as claimed in claim 8, wherein the one blank has a thickness of greater than 10 mm.

12. A process as claimed in claim 8, wherein the ceramic material comprises zirconium oxide.

13. A process as claimed in claim 8, wherein the one blank has a cylindrical form and the means for its force-locking clamping comprises concentric grooves.

* * * * *

UNITED STATES PATENT AND TRADEMARK OFFICE
CERTIFICATE OF CORRECTION

PATENT NO. : 7,604,759 B2  Page 1 of 1
APPLICATION NO. : 10/551838
DATED : October 20, 2009
INVENTOR(S) : Daniel Gubler et al.

It is certified that error appears in the above-identified patent and that said Letters Patent is hereby corrected as shown below:

On the Title page, Item (75) Inventors: Add --Arnold Wohlwend, Schellenberg, Liechtenstein--

Signed and Sealed this
Fifteenth Day of November, 2011

David J. Kappos
*Director of the United States Patent and Trademark Office*